United States Patent
Szczykutowicz

(10) Patent No.: US 11,995,831 B2
(45) Date of Patent: May 28, 2024

(54) METHOD AND APPARATUS FOR OPTIMIZING THE USE OF CONTRAST AGENTS DURING MEDICAL IMAGING

(71) Applicant: Wisconsin Alumni Research Foundation, Madison, WI (US)

(72) Inventor: Timothy P. Szczykutowicz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 509 days.

(21) Appl. No.: 17/226,198

(22) Filed: Apr. 9, 2021

(65) Prior Publication Data

US 2022/0327706 A1    Oct. 13, 2022

(51) Int. Cl.
*G06T 7/00* (2017.01)
*A61B 6/00* (2006.01)
*A61B 6/03* (2006.01)
*A61K 49/04* (2006.01)
(Continued)

(52) U.S. Cl.
CPC ............ *G06T 7/0016* (2013.01); *A61B 6/032* (2013.01); *A61B 6/5294* (2013.01); *A61K 49/0438* (2013.01); *A61M 5/007* (2013.01); *G06T 7/33* (2017.01); *G16H 10/60* (2018.01); *G16H 15/00* (2018.01); *G16H 30/40* (2018.01);
(Continued)

(58) Field of Classification Search
CPC ... G06T 7/0016; G06T 7/0012; G06T 7/0014; G06T 7/30; G06T 7/32; G06T 7/33; G06T 2207/10056; G06T 2207/10061; G06T 2207/10064; G06T 2207/10081; G06T 2207/10088; G06T 2207/10096; G06T 2207/30004; G06T 2207/30024; G16H 10/00; G16H 10/60; G16H 15/00; G16H 20/00; G16H 20/10; G16H 20/13; G16H 20/17; G16H 30/00; G16H 30/40; A61B 6/032; A61B 6/03; A61B 6/035; A61B 6/037; A61B 6/48; A61B 6/481; A61B 6/484; A61B 6/485; A61B 6/486; A61B 6/5294; A61K 49/0438; A61K 49/0433;
(Continued)

(56) References Cited

U.S. PATENT DOCUMENTS 5,687,208 A * 11/1997 Bae ............... G16H 20/17
378/8
8,699,770 B2    4/2014 Kemper et al.
(Continued)

FOREIGN PATENT DOCUMENTS

AU    2018202678 B2    5/2018
WO    2019219458 A1    11/2019

OTHER PUBLICATIONS

International Search Report for PCT/US2022/071302 dated Jul. 13, 2022.
(Continued)

*Primary Examiner* — Edward F Urban
*Assistant Examiner* — Duy Tran
(74) *Attorney, Agent, or Firm* — Boyle Fredrickson S.C.

(57) ABSTRACT

A method of establishing a quantitative measure of contrast enhancement in contrast medical imaging through computer analysis of baseline and enhanced images allows statistical comparison of protocols and imaging parameters from routine hospital operations to enhance and evaluate such protocols and parameters.

19 Claims, 4 Drawing Sheets

(51) Int. Cl.
*A61M 5/00* (2006.01)
*G06T 7/33* (2017.01)
*G16H 10/60* (2018.01)
*G16H 15/00* (2018.01)
*G16H 30/40* (2018.01)

(52) U.S. Cl.
CPC ............... *G06T 2207/10081* (2013.01); *G06T 2207/30004* (2013.01)

(58) Field of Classification Search
CPC ........... A61K 49/0447; A61K 49/0452; A61M 5/007; A61M 5/00
See application file for complete search history.

(56) References Cited

U.S. PATENT DOCUMENTS

| | | | |
|---|---|---|---|
| 2007/0127789 A1* | 6/2007 | Hoppel | A61B 6/5288 600/407 |
| 2007/0236491 A1* | 10/2007 | Hundley | A61B 6/466 345/418 |
| 2013/0211247 A1* | 8/2013 | Kalafut | A61B 6/507 703/11 |
| 2016/0128659 A1 | 5/2016 | Carton et al. | |
| 2018/0242917 A1 | 8/2018 | Bagherzadeh et al. | |
| 2019/0192091 A1 | 6/2019 | Lee et al. | |
| 2019/0313990 A1* | 10/2019 | Sahbaee Bagherzadeh | A61M 5/007 |
| 2019/0361081 A1 | 11/2019 | Liang et al. | |

OTHER PUBLICATIONS

Wang et al.; "Adaptation of Contrast Injection Protocol to Tube Potential for Cardiovascular CT." American Journal of Roentgenology 203, No. 6 (Dec. 2014): pp. 1181-1191. US.

Lilian Poh Poh Yap et al.; "Customised weight-based vol. contrast media protocol in CT of chest, abdomen and pelvis examination." Journal of Medical Imaging and Radiation Sciences (2021) pp. 1-8; CA.

* cited by examiner

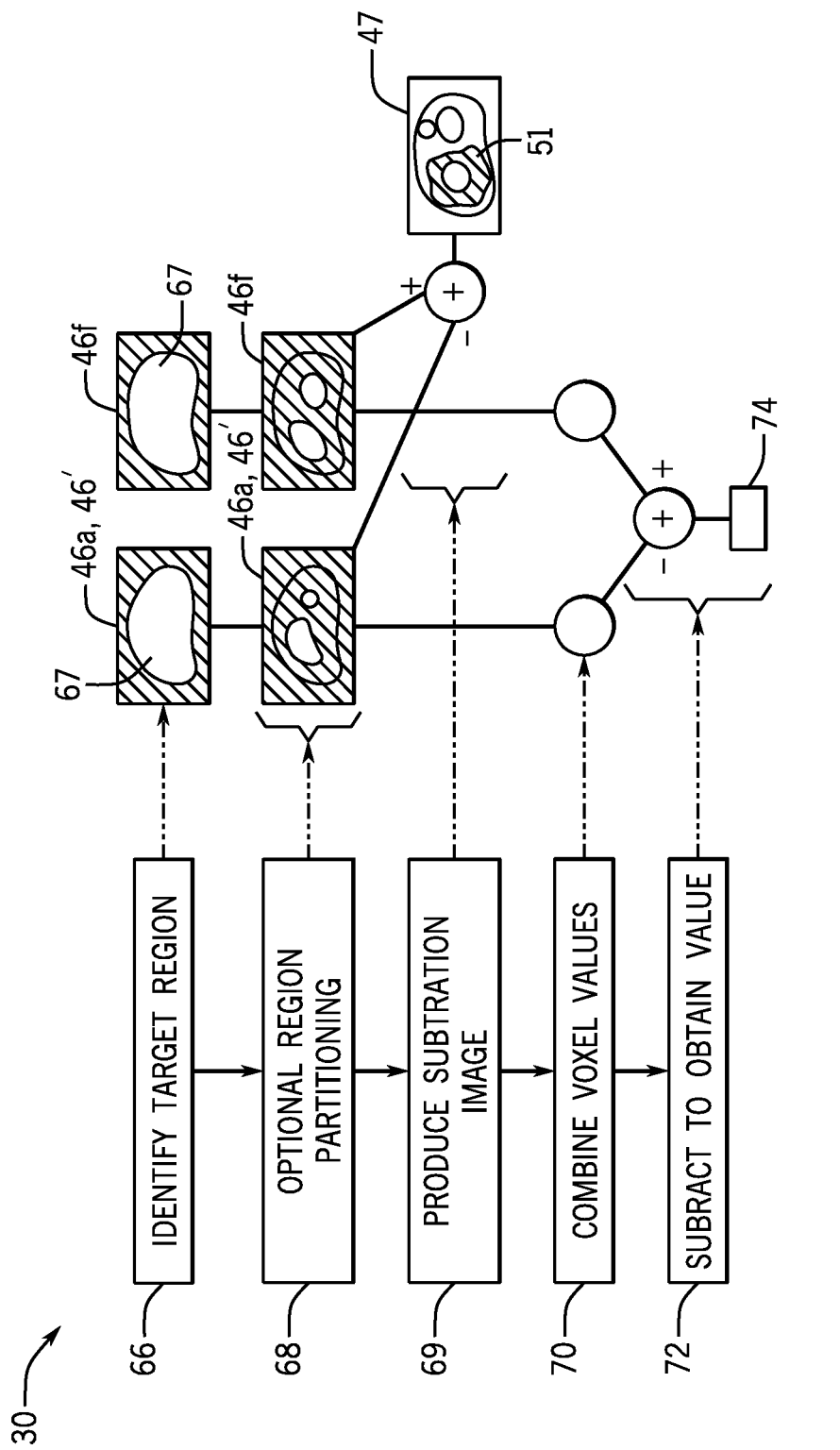

METHOD AND APPARATUS FOR OPTIMIZING THE USE OF CONTRAST AGENTS DURING MEDICAL IMAGING

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates to medical imaging devices such as computed tomography (CT) machines and, in particular, to a method and apparatus providing a quantitative evaluation of the use of contrast materials in such machines and the use of this quantitative evaluation to evaluate contrast protocols.

Volumetric medical imaging equipment, such as computed tomography machines, can collect image data over a volume of patient tissue, for example, in a set of adjacent "slices" taken through the patient, providing improved visualization of the internal anatomy of the patient. The ability to distinguish among different tissues within the patient using such equipment can be enhanced by using contrast agents, such as intravenous iodine materials in CT, that have preferential uptake in tissue or structures of interests. Such contrast materials, in CT, provide greater x-ray attenuation in high contrast uptake tissue, promoting improved visibility of the structures. Analogous contrast materials may be used in other volumetric imaging equipment such as magnetic resonance imaging equipment (MRI).

The successful use of contrast agents in volumetric imaging is guided by sophisticated contrast enhancing protocols describing the selection of a contrast agent, contrast agent volume, contrast agent how rate, and the contrast agent concentration. Such protocols may also indicate whether to use a saline flush volume after introduction of the contrast agent and may identify a preferred particular venous access location, cannula gauge size, and contrast agent temperature as well as recommended imaging machine settings including scan timing, scan speed, and scan beam energy.

Different contrast enhancing protocols may be used for different patient specific factors including cardiac output, weight, normal or abnormal vasculature, and the like.

Some parameters of the protocols (for example, the amount of delay after the introduction of contrast media as depends on a specific patient's cardiac output or vascular abnormalities or contrast injection parameters like flowrate or saline flush) may be adjusted or selected during the imaging process using a bolus tracking procedure in which progress of a bolus of contrast agent as it travels through the patient is monitored through a set of cine type images. In such a bolus tracking procedure, a baseline scan location (typically a slice) is identified in the relevant tissue to be enhanced with a contrast agent and a baseline scan prior to the introduction of contrast media is obtained. Repeated acquisitions at the same slice location are taken after injection of the contrast media to track the media's arrival in the tissue of interest. Once the bolus has arrived to properly infuse the tissue (for example, as detected automatically by an absolute increase in signal value the tissue) image data for a volume of tissue around the baseline scan is acquired.

Bolus tracking does not eliminate the need to make an ex ante selection of most protocol parameters and generally cannot fully compensate for sub optimal parameter selection. For example, bolus tracking does not eliminate the need to select a proper x-ray tube voltage or correct loss of enhancement associated with a sub optimal x-ray tube voltage or correct for the effects of patient weight. Sub optimal protocols can lead to excessive contrast material usage with increased costs and in some cases unnecessary risk to the patient. Unfortunately, the large number of protocol parameters makes it difficult to establish optimal protocols for a range of clinical situations through controlled experimentation.

SUMMARY OF THE INVENTION

The present invention provides a method of producing a quantified measure of image contrast enhancement for a variety of contrast enhanced image acquisitions. This quantified measure allows routine medical imaging data to be directly compared and thus statistically processed to identify optimal contrast imaging parameters, harnessing routine image acquisition into a set of experiments revealing how to improve contrast agent use. The measure of contrast enhancement may be made, in most cases, without the need to acquire additional scans of the patient, but by using scans obtained during conventional bolus tracking or from previous patient imaging.

In one embodiment, the invention provides a method for assessing contrast enhancement in medical images comprising:
  (a) acquiring, in a medical imaging procedure, enhanced volumetric data of tissue using a contrast agent;
  (b) acquiring baseline volumetric data of at least a portion of the tissue without enhancement by the contrast agent;
  (c) comparing the enhanced volumetric data and baseline volumetric data to generate a quantitative enhancement value representing an amount of image enhancement in the enhanced volumetric data referenced to the baseline volumetric data; and
  (d) generating a report linking the quantitative enhancement value to the medical imaging procedure.

It is thus a feature of at least one embodiment of the invention to provide a quantified measure of image enhancement using contrast agents that can be used alone (to evaluate the quality of acquisition) or as a reference point for assessing imaging protocols. It is another feature of at least one embodiment of the invention to provide an objective image enhancement measure executable on a computer without human intervention and thus having low cost to be practical for integration into normal healthcare services.

The baseline volumetric data may be a subset of the enhanced volumetric data. For example, the baseline volumetric data may be acquired during the medical procedure as a slice selected for bolus monitoring prior to acquisition of the enhanced volumetric data larger than the slice.

It is thus a feature of at least one embodiment of the invention to provide the desired quantitative measurement without requiring additional scans or dose to the patient or with minimal additional scans and dose. It is yet another feature of at least one embodiment of the invention to permit as little as a single slice of baseline data to be used to assess contrast enhancement in a multi-slice volume of image data of the contrast-enhanced tissue.

The baseline volumetric data may be registered to a corresponding volume of the enhanced volumetric data, and the comparison process may compare the baseline volumetric data to the corresponding volume of the enhanced volumetric data as registered.

It is thus a feature of at least one embodiment of the invention to permit the baseline data to be extracted from other scans of the patient not necessarily preregistered to the enhanced volumetric data or to accommodate slight patient movement between the acquisition of the baseline data and the larger volumetric data.

The registration may align voxels of the baseline volumetric data and enhanced volumetric data to minimize a difference between corresponding voxel values.

It is thus a feature of at least one embodiment of the invention to provide a robust and simple way of registering baseline and enhanced images without requiring consistent or preestablished fiducial reference points in the images.

The enhanced volumetric data may be acquired at different phases of contrast agent introduction and the enhanced volumetric data for each of the different phases may be compared to the baseline volumetric data to generate a quantitative enhancement value for each of the phases to generate a report for each of the phases linking the quantitative enhancement value to the medical imaging procedure.

It is thus a feature of at least one embodiment of the invention to provide assessment of multiphase image acquisitions and protocols used in those acquisitions.

The baseline volumetric data may be acquired from a database providing volumetric data of a same patient and same tissue taken prior to the medical procedure.

It is thus a feature of at least one embodiment of the invention to leverage the ability to use a single or limited number of slices for the baseline image to allow the baseline image to be acquired from other non-contemporaneous images of the patient.

The quantitative enhancement value may be produced by determining a difference derived from values of the voxels of the enhanced volumetric data applied against values of the voxels of the baseline volumetric data.

It is thus a feature of at least one embodiment of the invention to provide a simple measurement of enhancement by a subtraction process either before or after values of the voxels have been manipulated in other ways.

In addition, or alternatively, the quantitative enhancement value may be produced by combining together values derived from multiple voxels of the enhanced volumetric data and multiple values of the baseline volumetric data.

It is thus a feature of at least one embodiment of the invention to provide a single simple quantitative enhancement value for assessing contrast enhancement.

In addition, or alternatively, the quantitative enhancement value may be produced by an effective scaling of values derived from the voxels of the enhanced volumetric data and baseline volumetric data according to the number of voxels to normalize the quantitative enhancement value to volume.

It is thus a feature of at least one embodiment of the invention to allow the production of a quantitative enhancement value that may be compared among images having different scaling or amount of contrast-enhanced tissue.

In addition, or alternatively, the quantitative enhancement value may be produced by disregarding (attenuating or nulling to zero) values derived from voxels of the enhanced volumetric data and baseline volumetric data where enhancement has not occurred.

It is thus a feature of at least one embodiment of the invention to increase the sensitivity of the quantitative enhancement value by isolating enhanced from unenhanced tissue.

The method may further repeat (a)-(c) for multiple medical imaging procedures having at least one different parameter, and (d) may provide an indication of quantitative enhancement value as a function of the different parameters.

It is thus a feature of at least one embodiment of the invention to allow contrast protocols to be evaluated and compared through the agency of the quantitative enhancement value.

The parameter being evaluated may, in some cases, be patient weight and patient cardiac output.

It is thus a feature of at least one embodiment of the invention to allow evaluation of contrast protocols based on pre-characterizable patient qualities to provide more accurate bolus tracking or to optimize parameters that are not addressable through bolus tracking.

Alternatively, the parameter being evaluated may be different practice groups of multiple physicians.

It is thus a feature of at least one embodiment to allow the evaluation of multiparameter protocols often associated with physician groups.

Alternatively, the parameter being evaluated may be scan settings of a medical imaging machine used for acquiring the enhanced volumetric data.

It is thus a feature of at least one embodiment of the invention to allow assessment of optimal imaging machine settings for contrast enhancement.

In some cases, the parameter being evaluated may be a cost of contrast agent.

It is thus a feature of at least one embodiment of the invention to help reduce medical procedure costs.

In some cases, the parameter being evaluated may be a protocol for the injection of contrast media.

It is thus a feature of at least one embodiment of the invention to provide a method of optimizing the parameters related to delivery of contrast media, for example, flow rate, volume, etc.

These particular objects and advantages may apply to only some embodiments falling within the claims and thus do not define the scope of the invention.

BRIEF DESCRIPTION OF THE. DRAWINGS

FIG. 7 is a detailed flowchart of the step of comparison of the flowchart of FIG. 3.

DETAILED DESCRIPTION OF THE PREFERRED EMBODIMENT

Hardware Overview

Figure 1:
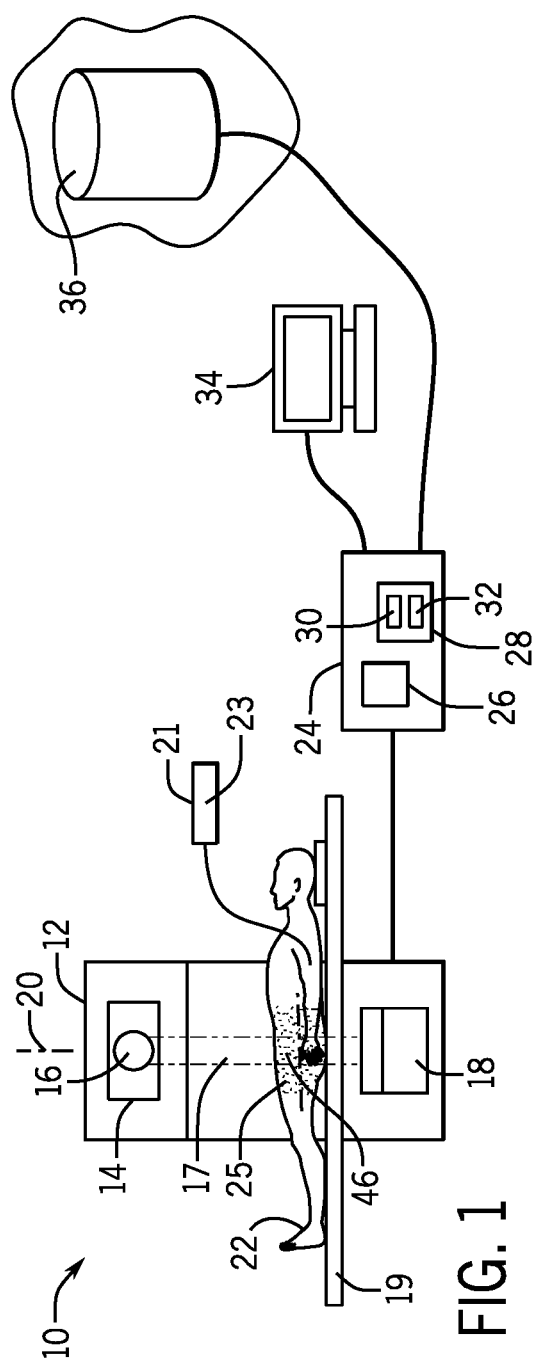
FIG. 1 is a simplified block diagram of an imaging apparatus including a CT machine and associated electronic computer and terminal, the latter in communication with a data archiving system such as a PACS (picture archiving and communication system)

Referring now to FIG. 1, an imaging system 10 suitable for practice of the present invention may include a medical imaging machine 12, such as a CT scanner of the type providing an internal rotating gantry 14 holding an x-ray tube 16 in opposition to an x-ray detector 18 for rotation in a plane 20 about a patient 22 supported on a patient table 19. The x-ray tube 16 and x-ray detector 18 cooperate to acquire data along a slice 17 through the patient. Movement of the patient table 19 allows multiple slices 17 to be assembled together to acquire a volume 25 of data of the patient 22.

A contrast media injector 21 holding a contrast agent 23 may be positioned near the medical imaging machine 12 for the delivery of a contrast media intravenously to the patient 22 during the scanning process.

Generally, the imaging machine 12 may be associated with a computer 24 having a processor 26 and associated memory 28, the latter holding a program 30 implementing features of the present invention and data files 32 representing data collected from the imaging machine 12 during slice acquisition. These data files 32 will be comprised of multiple values (for example, Hounsfield units) for different voxels representing volume elements in the patient as understood in the art.

The computer 24 may be associated with a terminal 34, for example, providing for graphic outputs such as a report or the like and allowing user input as necessary. In addition, the computer 24 may communicate with a central database 36 holding other data files 32 indexed by a patient identifier permitting storage and retrieval of such data files 32. The central database 36 may, for example, be a PACS system as is generally understood in the art.

While a CT machine has been depicted, it will be appreciated that the invention is applicable to patient image data obtained on other modalities of imaging machines such as magnetic resonance imaging machines and the like.

Hardware Operation

Figure 2:
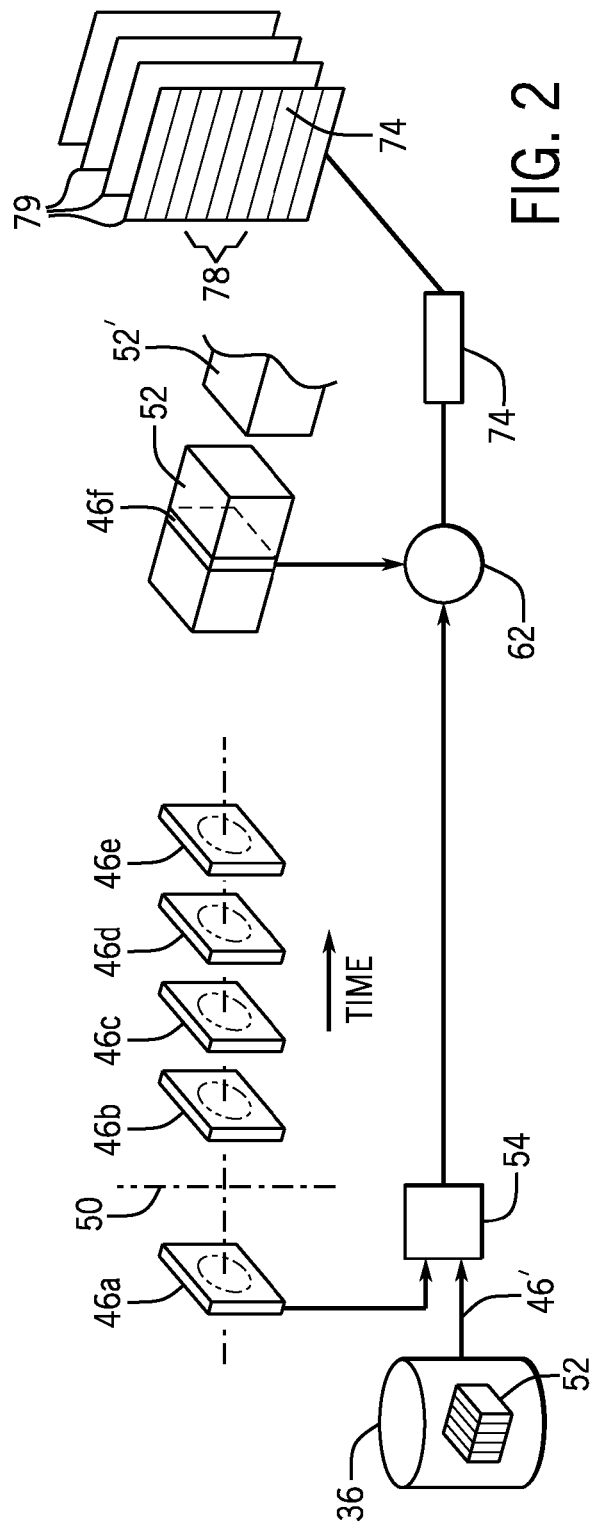
FIG. 2 is a data flow diagram showing the acquisition of image data obtained, for example, during bolus tracking using the CT machine of FIG. 1, and processing of that image data for the generation of a quantitative enhancement value assessing the quality of the acquired image data.
Figure 3:
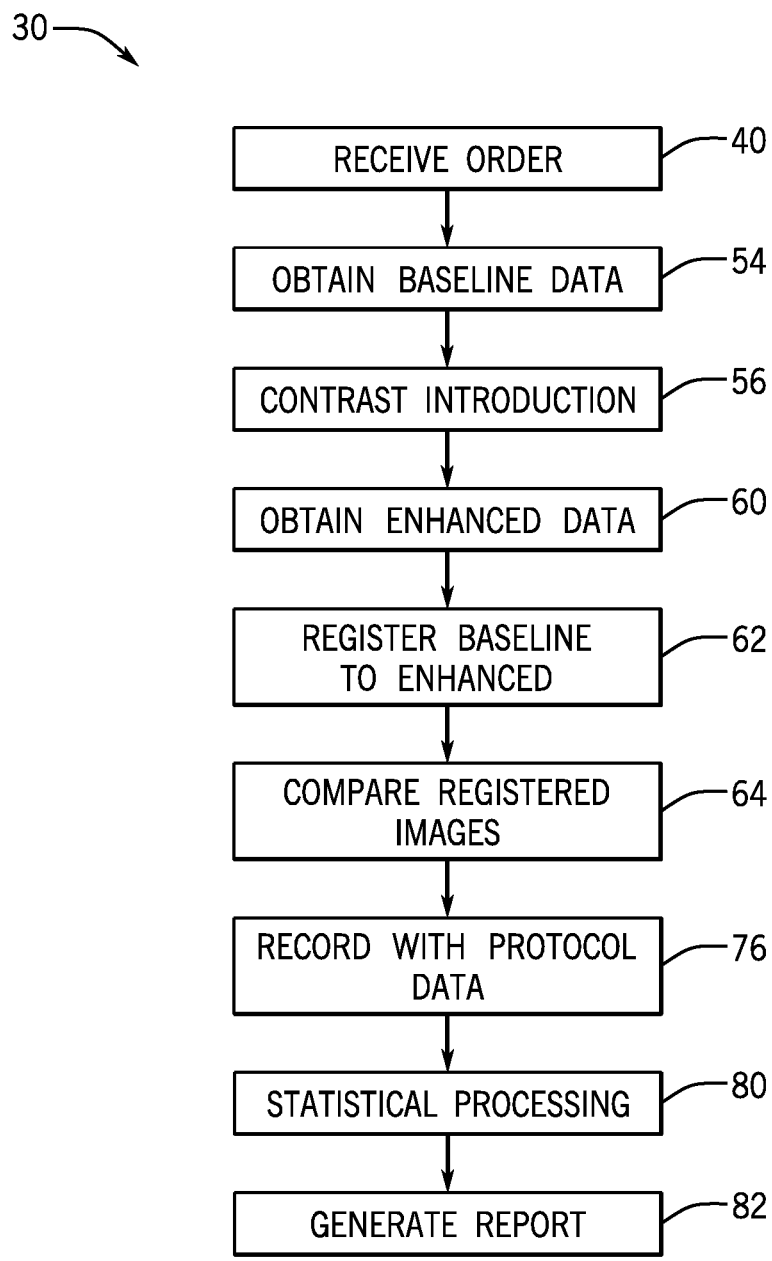
FIG. 3 is a flowchart of a program executed by the electronic computer of FIG. 1 in generating the quantitative enhancement value of FIG. 2.

Referring now also to FIGS. 2 and 3, the program 30 may be invoked upon receiving an order indicated by process block 40 for an imaging study of the patient 22 and involving the injection of contrast media 23 from the injector 21. Such an order will normally be generated by a physician and will include a patient identifier and associated imaging protocol (protocol 78 described below) either contained in or referenced to the order. Such a protocol 78 may include multiple parameters or settings such as those describing: contrast agent type, contrast agent total volume, contrast agent flow rate, contrast agent concentration, saline flush volume, venous access location, contrast delivery cannula gauge, contrast agent viscosity, contrast agent temperature, scan timing with respect to contrast agent introduction, scan speed of the imaging machine, scan beam energy, and patient specific factors including patient cardiac output, patient weight, patient abnormal vs. normal vasculature, as well as site/machine identifying information including physician groups and group protocols.

In one example, the protocol may implement a bolus tracking procedure, depicted generally in FIG. 2, where a first baseline slice image data 46a is acquired of the patient 22 prior to injection of the contrast media 23. This baseline slice image data 46a is selected to be located in tissue of clinical significance where contrast enhancement is desired and typically represents a cross-sectional volume of the patient taken along the transverse plane and having a width of less than or equal to 10 mm although the invention contemplates other widths for example less than 80 mm may also be useful. After contrast media is injected at a first time 50 (represented by process block 56) a set of sequential slice images 46b-46d of the same region as the baseline slice image data 46a may be taken at regular successive time intervals in order to track movement of a bolus of contrast material 23 into the tissue of the patient 22. Either by observation or by an automatic monitoring of a contrast level reaching a predetermined threshold, full volume image data 52 is acquired, for example, having a width of many tens of centimeters and embracing slice image data 46f corresponding in location to the baseline slice image 46a as indicated by process block 60.

Referring still to FIGS. 1, 2, and 3, at process block 62, the baseline slice image data 46a is registered with a corresponding slice image data 46f from the volume 52 for comparison of the two. This registration is straightforward in the case where baseline slice image data 46a and corresponding slice image data 46f are part of a single bolus acquisition procedure as described above and can rely initially on the intrinsic positioning capabilities of the imaging machine 12 monitoring the relative position between the patient table 19 on which the patient 22 lies and the position of the plane 20 describing a slice 17 being acquired. Nevertheless, the possibility of patient motion, either with respect to the table 19 or at a fixed position on the table 19 and caused by physiological processes such as breathing, is further addressed through an additional registration process. This registration process adjusts the relative positioning of the slice image data 46a and 46f to maximize a matching of corresponding voxels in the different slices. Such registration processes generally operate to minimize cumulative differences between corresponding voxels and may employ the registration process described, for example, Hill, D. L., Batchelor, P. G., Holden, M., & Hawkes, D, J. (2001), "Medical image registration", Physics in medicine & biology, 46(3), R1 hereby incorporated by reference.

In an alternative embodiment, baseline slice image data 46' may be acquired from the database 36 at process block 54 described above. In this case, a previous scan of the patient 22 matching the patient identification number in the order received at process block 40 may be selected along with slice image data 46' from that scan. This selection process may be either by the operator of the imaging machine 12 or on an automatic basis by matching data from the order 40 with PACs image index data on an automatic or semiautomatic basis. The registration process may then compare that baseline slice image data 46' with multiple slices in the volume 52 to find a corresponding best match slice in enhanced slice image data 46f using the registration process applied sequentially to a set of different slices of the enhanced slice image data 46f and comparing the registration fit values produced during that registration process.

In both cases, using either the baseline slice image data 46a or baseline slice image data 46', at succeeding process block 64, the baseline slice image data 46a/46' is then compared to the enhanced slice image data 46f to produce a quantified contrast enhancement value characterizing how well the contrast agent 23 has worked under the given protocol to enhance the data of the slice image data 46f.

Referring now also to FIG. 7, at a first step of this comparison of process block 64, indicated by process block 66, a region of analysis is identified being a subset of the entire slice. In one embodiment, the region may be identified as an organ (either by healthcare professional input or by an automatic extraction from the received order at process block 40). Well understood segmentation techniques such as described in Graffy, P. M., Sandfort, V Summers, R. M., & Pickhardt, P. J., (2019), "Automated liver fat quantification at nonenhanced abdominal CT for population-based steatosis assessment," Radiology, 293(2), 334-342, (incorporated by reference) may then be used to isolate the organ as a region of analysis 67 to which subsequent analysis will be applied. By removing this data more sensitive enhancement assessments may be made although the invention contemplates in some instances that the entire slice image may be used as a rough region of analysis 67.

Next at process block 68, an optional sub partitioning of the region of interest may be performed. For example, a thresholding and segmentation process may be used to remove air and bone from the image data of the baseline slice image data 46a/46' and the enhanced slice image data 46f in cases where these tissues are unlikely to represent meaningful enhancement data. In addition, or alternatively, each voxel of the baseline slice image data 46a/46' may be compared to a corresponding registered voxel of the enhanced slice image data 46f to see if there is any enhancement. Enhancement would be represented by a positive (nonzero) difference in corresponding Hounsfield numbers. In this case, all other voxels (representing no enhancement or negative enhancement) may be removed, for example, using a masking technique. This step of distinguishing enhanced voxels may also be employed to provide useful data to the healthcare professional with respect to the proportion of enhanced versus unenhanced voxels that can provide insight into treatment contrast efficacy in which can be included in the reports described below with respect to process block 82 to be described.

At next process block 69, a subtraction image 47 may be generated by subtracting the baseline slice image data 46a/46' on a voxel by voxel basis from corresponding voxels of the enhanced slice image data 46f. The resulting subtraction image 46 indicates both the location and the degree of enhancement of the tissue isolated from variations in brightness values of the image reflected in the underlying baseline image 46a and 46' in a manner analogous to digital subtraction angiography. The resulting areas 51 showing enhancement may be quantified, for example, using methods method like standard deviation or texture analysis and mapped to colors or legend values to provide more information to the healthcare professional.

At succeeding process block 70, the values of the voxels of each of the baseline slice image data 46/46' and enhanced slice image data 46f are separately combined, for example, by taking a median of the voxel values. As will be understood in the art, this process of taking a median value essentially normalizes the values of the voxels to volume by dividing the sum of the voxel values by the number of voxels and thus isolates the resulting value from variations caused by different numbers of voxels as opposed to different levels of enhancement.

At process block 72 the median value from the baseline slice image data 46/46' is subtracted from the median value of the enhanced slice image data 46f to produce a single number representing the quantitative enhancement value 74 of the present invention.

Note generally that because of the commutative properties of many of these above described operations, the strict ordering may be changed of process blocks 66-72 to produce the same result and accordingly the step should not be considered as necessarily requiring performance of these process blocks in this order.

Referring again to FIGS. 2 and 5, at process block 76 the quantitative enhancement value 74 is stored with the protocol 78 received process block 40 as part of the patient record. The protocol 78 referred to in this context is described above with respect to process block 40.

Process blocks 40, 54, 56, 60, 62, 64 and 76 described with respect to FIG. 3 may be repeated for multiple patients 22 in the normal course of hospital operations to generate multiple records 79 recording associated protocol 78 and the quantitative enhancement value 74. As indicated by process block 80 of FIG. 3, this data they may then be subject to statistical processing to expose correlations and relationships between the quantitative enhancement value 74 and individual or multiple of the parameters of the protocol 78 across many patients 22. Such processing, for example, may fit trendlines to scatterplots having points distributed in dimensions of the quantitative enhancement value 74 and one or more protocol parameters. The trendlines show the underlying relationships between particular parameters and the quantitative enhancement value 74 revealing a course of possible protocol improvement with respect to changes in the parameters. Each of these analyses may be presented in one or more reports displayed on terminal 34 shown in FIG. 1 and as indicated by process block 82 of FIG. 3.

Figure 4:
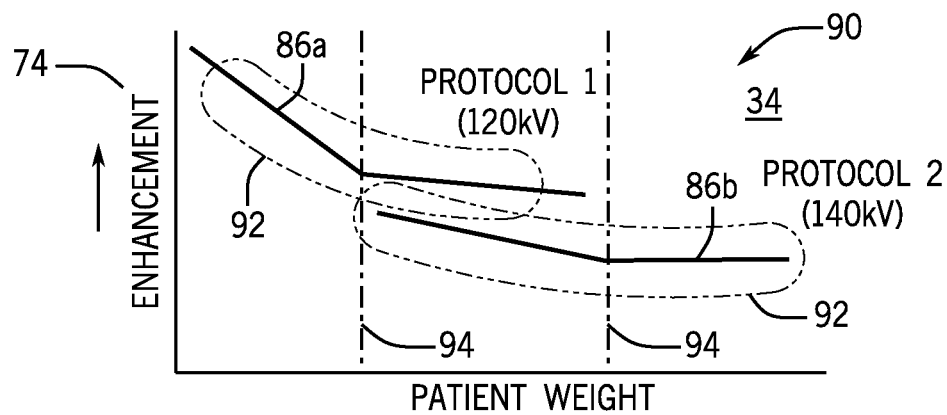
FIG. 4 is a representation of a first report produced by the present invention correlating image enhancement quality with patient weight for two different protocols.

Referring now to FIG. 4, in one example investigated by the present inventor, quantitative enhancement value 74 (indicated in the vertical axis) may be evaluated against the parameter of patient weight to produce trendlines 86a and 86b of a report plot 90. Trendline 86a may be associated with a first additional protocol parameter representing a setting of the medical imaging machine 12 (a CT scanner) to a 120 kV x-ray tube voltage whereas trendline 86b may represent an x-ray tube voltage of 140 kV. Each of the trendlines 86 may be established through a curve fitting of a set of data points 92 associated with different patients or different medical procedures as part of the routine delivery of medical care. The trendlines 86 in this case provide insight into the fact that for a particular range of patient weights between weight lines 94, improved contrast is obtained with the first protocol using an x-ray tube voltage of 120 kV per trendline 86a. It will be appreciated that other characteristics of the patient may be used for example discrete categorizations of cardiac output from previous contrast enhanced studies. Generally, the horizontal axis could categorize any known disease processes such as documented liver or kidney disease.

Figure 5:
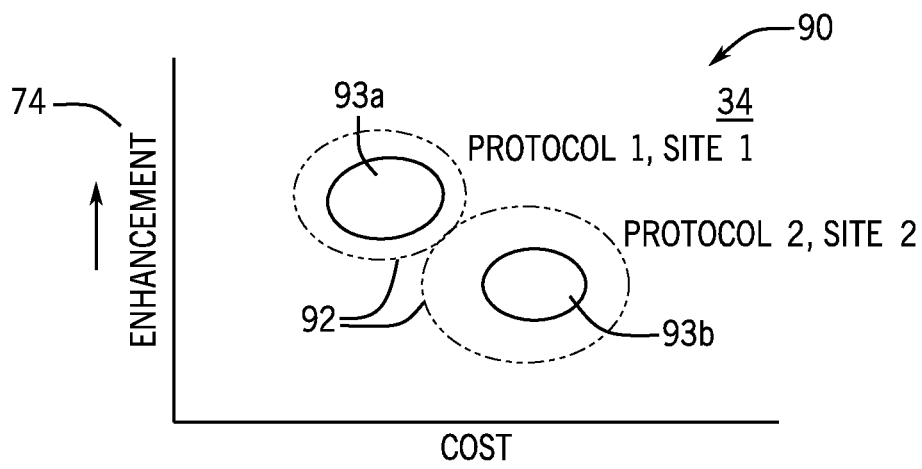
FIG. 5 is a figure similar to that of FIG. 4 showing a report relating image quality protocol and cost.
Figure 6:
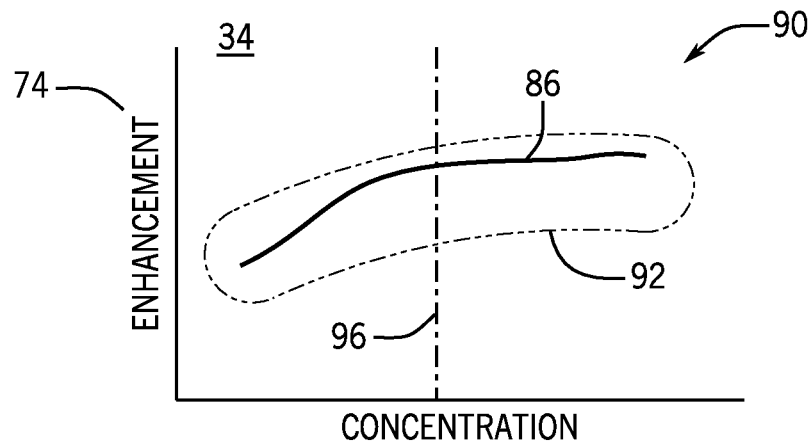
FIG. 6 is a figure similar to FIGS. 4 and 5 showing a report relating image quality to flow rate of the contrast media during introduction into the patient.

Referring now to FIG. 5, an alternative report may provide a plot 90 of quantitative enhancement value 74 on the vertical axis versus contrast agent cost on the horizontal axis. Data points 92 may be collected for imaging using a first protocol at a first site with a first group of physicians (grouping 93a) and for imaging using a second protocol at a second site with a second group of physicians (grouping 93b). Such a report may reveal the potential for decreasing contrast volumes and therefore lowering costs for smaller patients by lowering their enhancement equivalent to larger patients where such a change would provide uniformity in enhancement across patient size Referring now to FIG. 6, an alternative plot. 90 for a report may be similarly prepared by plotting quantitative enhancement value 74 on the vertical axis versus a contrast agent delivery parameter, in this concentration, on the horizontal axis. Again, a trendline 86 may be fit to data points 92 to reveal a possibly optimal concentration 96 using data collected during normal provision of healthcare to optimize contrast parameters.

Referring again to FIG. 2, it will be appreciated that the processes of process blocks 40, 54, 56, 60, 62, 64, 76, 80, and 82 may be performed not merely between a baseline slice image data 46a/46' and slice image data 46f of volume 52 but also between this baseline slice image data 46a/46' and a series of subsequent volumes 52', for example, in a multiphase study including, for example, one having an arterial phase, a late arterial phase, and a parenchymal phase, at a final acquisition each separated by tens of seconds or minutes.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

I claim:

1. A method for assessing contrast enhancement in medical images comprising:
   (a) acquiring, in a medical imaging procedure and according to a parameter, enhanced volumetric data of tissue using a contrast agent;
   (b) acquiring baseline volumetric data of at least a portion of the tissue without enhancement by the contrast agent and according to the parameter;
   (c) comparing the enhanced volumetric data and baseline volumetric data to generate a quantitative enhancement value representing an amount of image enhancement in the enhanced volumetric data referenced to the baseline volumetric data; and
   (d) generating a report linking the quantitative enhancement value to the medical imaging procedure; and
   further repeating (a)-(c) for multiple different medical imaging procedures having different parameters and wherein (d) provides an indication of quantitative enhancement value as a function of changes in the parameter.

2. The method of assessing contrast enhancement of claim 1 wherein the baseline volumetric data is a subset of the enhanced volumetric data.

3. The method of assessing contrast enhancement of claim 2 wherein the baseline volumetric data is acquired during the medical procedure as a slice selected for bolus monitoring prior to acquisition of the enhanced volumetric data.

4. The method of assessing contrast enhancement of claim 1 wherein the baseline volumetric data is registered to a corresponding volume of the enhanced volumetric data and the comparison process compares the baseline volumetric data to the corresponding volume of the enhanced volumetric data as registered.

5. The method of assessing contrast enhancement of claim 4 wherein the registration aligns voxels of the baseline volumetric data and enhances volumetric data to minimize a difference between corresponding voxel values.

6. The method of assessing contrast enhancement of claim 1 wherein enhanced volumetric data is acquired at different phases of contrast agent introduction;
   wherein the enhanced volumetric data for each of the different phases is compared to the baseline volumetric data to generate a quantitative enhancement value for each of the phases; and
   a report is generated for each of the phases linking the quantitative enhancement value to the medical imaging procedure.

7. The method of assessing contrast enhancement of claim 1 wherein the baseline volumetric data is acquired from a database providing volumetric data of a same patient and same tissue taken prior to the medical procedure.

8. The method of assessing contrast enhancement of claim 1 wherein the quantitative enhancement value is produced by determining a difference derived from values of voxels of the enhanced volumetric data applied against values of voxels of the baseline volumetric data.

9. The method of assessing contrast enhancement of claim 1 wherein the quantitative enhancement value is produced by combining together values derived from multiple voxels of the enhanced volumetric data and multiple values of the baseline volumetric data.

10. The method of assessing contrast enhancement of claim 1 wherein the quantitative enhancement value is produced by an effective scaling of values derived from voxels of the enhanced volumetric data and voxels of the baseline volumetric data according to a number of voxels to normalize the quantitative enhancement value to volume.

11. The method of assessing contrast enhancement of claim 1 wherein the quantitative enhancement value is as a function of the relative number of voxels of the enhanced volumetric data where enhancement has occurred and has not occurred.

12. The method of assessing contrast enhancement of claim 1 wherein the at least one different parameter is selected from the group consisting of patient weight and predetermined classifications of patient disease progression.

13. The method of assessing contrast enhancement of claim 1 wherein the at least one different parameter is a practice group of multiple physicians.

14. The method of assessing contrast enhancement of claim 1 wherein at least one different parameter is a setting of a medical imaging machine used for acquiring the enhanced volumetric data.

15. The method of assessing contrast enhancement of claim 1 wherein the at least one different parameter is cost of contrast agent.

16. The method of assessing contrast enhancement of claim 1 wherein at least one different parameter is a protocol for an injection of contrast media.

17. The method of assessing contrast enhancement of claim 1 wherein the enhanced volumetric data and baseline volumetric data are acquired with a computed tomography machine, wherein the contrast agent includes iodine, and the volumetric data is Hounsfield units.

18. The method of assessing contrast enhancement of claim 1 further including:

(e) subtracting the baseline volumetric data from the enhanced volumetric data to generate difference image indicating location and degree of image enhancement in the enhanced volumetric data.

19. A system for assessing contrast enhancement in medical images comprising:

a medical imaging machine;

a contrast injector adapted for an injection of a contrast material in a patient during scanning in the medical imaging machine; and electronic computer executing a stored program stored in non-transitory medium to:

(a) receive from the medical imaging machine, in a medical imaging procedure and according to a parameter, enhanced volumetric data of tissue using a contrast agent;

(b) acquire baseline volumetric data of at least a portion of the tissue without enhancement by the contrast agent and according to the parameter;

(c) compare the enhanced volumetric data and baseline volumetric data to generate a quantitative enhancement value representing an amount of image enhancement in the enhanced volumetric data referenced to the baseline volumetric data;

(d) generate a report linking the quantitative enhancement value to the medical imaging procedure; and further repeating (a)-(c) for multiple medical imaging procedures having at least one different parameter and wherein (d) provides an indication of quantitative enhancement value as a function of the different parameter.

* * * * *